US009658102B2

(12) United States Patent
Kustermans et al.

(10) Patent No.: US 9,658,102 B2
(45) Date of Patent: May 23, 2017

(54) METHOD AND SYSTEM FOR DETERMINING ULTRAVIOLET FLUENCE RECEIVED BY A FLUID

(71) Applicant: Trojan Technologies, London (CA)

(72) Inventors: Mark Adrian Kustermans, Strathroy (CA); Michael Sasges, Victoria (CA); Ankit Patras, Guelph (CA); Trisevgeni Trissa Kantzas, Guelph (CA)

(73) Assignee: Trojan Technologies, London, Ontario (CA)

( * ) Notice: Subject to any disclaimer, the term of this patent is extended or adjusted under 35 U.S.C. 154(b) by 0 days.

(21) Appl. No.: 15/036,962

(22) PCT Filed: Nov. 12, 2014

(86) PCT No.: PCT/CA2014/000800
§ 371 (c)(1),
(2) Date: May 16, 2016

(87) PCT Pub. No.: WO2015/070319
PCT Pub. Date: May 21, 2015

(65) Prior Publication Data
US 2016/0258811 A1 Sep. 8, 2016

Related U.S. Application Data
(60) Provisional application No. 61/962,758, filed on Nov. 15, 2013.

(51) Int. Cl.
G01N 21/01 (2006.01)
G01N 21/64 (2006.01)
(Continued)

(52) U.S. Cl.
CPC ............. *G01J 1/58* (2013.01); *A61L 2/0005* (2013.01); *A61L 2/10* (2013.01); *G01J 1/429* (2013.01);
(Continued)

(58) Field of Classification Search
USPC ....... 250/372, 373, 383, 390.07, 428, 432 T, 250/458.1, 459.2, 461.1, 461.2, 472.1,
(Continued)

(56) References Cited

U.S. PATENT DOCUMENTS 6,377,842 B1 4/2002 Pogue et al.
6,815,656 B1 * 11/2004 Lauer .................... H01S 5/5018
250/214 LA
(Continued)

FOREIGN PATENT DOCUMENTS

WO 03/007998 1/2003
WO 2013/138159 9/2013

OTHER PUBLICATIONS

PCT International Search Report dated Mar. 11, 2015 for PCT Patent Application No. PCT/CA2014/000800.

*Primary Examiner* — Bernard Souw
(74) *Attorney, Agent, or Firm* — Michael Stanley Tomsa; McAndrews, Held & Malloy, Ltd.

(57) ABSTRACT

There is described a method of determining the UV fluence received by a fluid. The method comprises the steps of: (a) irradiating the fluid at an unknown UV fluence; (b) measuring the fluorescence of a test sample of the fluid after irradiation in Step (a) to produce a test signal proportional to the concentration of a prescribed fluorescent composition of matter comprised in the test sample; and (c) determining the value of the unknown UV fluence by comparing the test signal to a calibration curve of a control signal proportional to concentration of the prescribed fluorescent composition of (Continued)

matter in the fluid as a function of applied UV fluence. There is also described a system for determining the UV fluence received by a fluid being treated in UV fluid treatment system comprising at least one UV source. The system comprises: (a) a radiation-transparent vessel for receiving a test sample of the fluid after irradiation of the fluid at an unknown UV fluence; (b) a fluorometer for measuring the fluorescence of the test sample received in the radiation-transparent vessel to produce a test signal proportional to the concentration of a prescribed fluorescent composition of matter comprised in the test sample; and (c) a controller configured to determine the value of the unknown UV fluence by comparing the test signal to a calibration curve of a control signal proportional to concentration of the prescribed fluorescent composition of matter in the fluid as a function of applied UV fluence.

20 Claims, 2 Drawing Sheets

(51) Int. Cl.
| | | |
|---|---|---|
| G01N 33/483 | (2006.01) | |
| C02F 1/32 | (2006.01) | |
| G01J 1/58 | (2006.01) | |
| A61L 2/10 | (2006.01) | |
| G01J 1/42 | (2006.01) | |
| G01N 33/15 | (2006.01) | |
| G01N 33/49 | (2006.01) | |
| C02F 1/00 | (2006.01) | |
| A61L 2/00 | (2006.01) | |

(52) U.S. Cl.
CPC ............. G01N 21/64 (2013.01); G01N 33/15 (2013.01); G01N 33/4833 (2013.01); G01N 33/49 (2013.01); A61L 2/0047 (2013.01); A61L 2202/11 (2013.01); C02F 1/008 (2013.01); C02F 1/32 (2013.01); G01N 2201/13 (2013.01)

(58) Field of Classification Search
USPC ......... 250/473.1, 483.1, 484.2, 486.1, 492.1, 250/504 R, 526, 581, 586; 600/476, 310, 600/312, 329, 342, 317; 356/51, 317, 356/320, 451, 450, 243.1, 243.5, 243.8, 356/246, 256; 436/172, 171, 164, 183, 436/800; 607/88, 94; 422/24
See application file for complete search history.

(56) References Cited

U.S. PATENT DOCUMENTS

| | | | |
|---|---|---|---|
| 7,993,580 B2 | 8/2011 | Anderle et al. | |
| 2010/0314551 A1* | 12/2010 | Bettles | C02F 1/32 250/432 R |
| 2010/0331927 A1 | 12/2010 | Cottrell et al. | |
| 2012/0168641 A1* | 7/2012 | Lizotte | A23L 3/28 250/435 |
| 2014/0028998 A1* | 1/2014 | Kaye | G01J 3/02 356/51 |

* cited by examiner

METHOD AND SYSTEM FOR DETERMINING ULTRAVIOLET FLUENCE RECEIVED BY A FLUID

CROSS-REFERENCE TO RELATED APPLICATION

The present application is a National Phase Entry of PCT International Application No. PCT/CA2014/000800, which was filed on Nov. 12, 2014, and claims the benefit under 35 U.S.C. §119(e) of provisional patent application Ser. No. 61/962,758, filed Nov. 15, 2013, the contents of which are hereby incorporated by reference.

BACKGROUND OF THE INVENTION

Field of the Invention

In one of its aspects, the present invention relates to a method for quantifying the ultraviolet (UV) fluence received by a fluid. In another of its aspects, the present invention relates to a method for UV treatment of a fluid containing a fluorescent composition of matter. In another of its aspects, the present invention relates to a method for UV treatment of cell culture media. In another of its aspects, the present invention relates to a method for UV treatment of culture media used in the production of biopharmaceuticals. In another of its aspects, the present invention relates to a method for UV treatment of fluids used in the purification of biopharmaceuticals. In another of its aspects, the present invention relates to a system for determining the UV fluence received by a fluid being treated in a UV fluid treatment system.

Description of the Prior Art

Ultraviolet (UV) radiation is commonly used to disinfect many types of fluid media by inactivating microorganisms such as bacteria, protozoa and viruses that may be present in those fluids. This type of sterilization is favorable as a non-thermal and non-adulterating process and is used in various industries and applications, including in the biopharmaceutical industry.

While UV irradiation has been used in the biopharmaceutical industry for packaging and surface sterilization applications, its application to cell culture media as a sterilization method has been very limited elsewhere. Production growth media or culture media are liquids comprising complex mixtures of amino acids, sugar, vitamins and other compounds designed to support the growth of microorganisms or cells.

Determining the UV fluence received by a fluid is important to ensure that an effective dose (also referred to throughout this specification as "fluence") of UV radiation has been received by the fluid to effectively inactivate the microorganisms present in the fluid. If too little UV radiation is received by the fluid, microorganisms in the fluid will not be inactivated to the extent required. Alternatively, certain fluid media may not tolerate over-irradiation and may be damaged if the UV fluence is not relatively precise.

Generally, UV radiation is applied to a fluid via UV emitters (e.g., UV lamps and the like) provided in a fluid treatment zone of a flow-through reactor. The UV fluence applied to a fluid in such a flow-through reactor is a function of, for example, the reactor design, lamp output, flow rate, as well as properties of the fluid itself (such as turbidity or opacity).

There are several known methods to measure the UV fluence in such flow-through reactors. One method consists of monitoring the UV source output (lamp intensity), optical absorbance and flow rate of the fluid to estimate UV fluence. This method has the disadvantage of being an indirect measure of UV fluence received by the fluid, and also is one which is not capable of accounting for non-uniform UV source output, blocked or non-uniform flow paths within the reactor, and is further dependent on accurate flow rate measurements.

UV actinometry is a known method to quantify the amount of UV radiation applied to a fluid. According to typical actinometric techniques, an exogenous UV-sensitive compound with a known quantum yield is added to the fluid at a concentration sufficient to absorb all incident photons. The UV-sensitive compound undergoes a UV-induced chemical change. The concentration of the photo-product produced by application of UV radiation to the UV sensitive compound is then measured. Together with the known quantum yield, the photo-product concentration can be used to quantify the absorbed UV radiation. Common, known UV actinometers include the ferrioxylate actinometer and the iodide/iodate actinometer.

Such exogenous actinometry solutions can be passed through a UV reactor before or after treatment of the target fluid in order to determine the UV fluence before or after the treatment, but cannot determine the UV fluence during treatment without changing the fluid composition.

U.S. Pat. No. 7,993,580 [Anderle et al. (Anderle)] purportedly addresses this limitation of conventional exogenous actinometric techniques through the use of a separate flow path with a thin layer of actinometry solution in a UV reactor, and using the measured change in the chemistry of the actinometer to control the reactor. However, this method requires a separate flow path for the actinometry solution to prevent contamination of the process fluid, and therefore does not measure the dose actually delivered to the process fluid. The separate flow path of the method taught by Anderle introduces complexity and uncertainty by both requiring a separate flow path and by not directly measuring the UV fluence applied to the process fluid itself.

International Publication Number WO 2003/007998 [Li et al.] teaches a method of monitoring UV irradiation of a fluid containing protein through changes in optical absorbance at 314 nm. This method has limited sensitivity. Absorbance measurements suffer from interference from other compounds. Many constituents in growth media will contribute to the absorbance at 314 nm (or any other wavelength). Therefore, there is an increased likelihood that changes in absorbance of one compound will be masked by absorbance of other compounds that do not change with UV dose.

The photochemistry of pure actinometry methods can be well characterized, but such methods become considerably more complicated when the fluid is a complex mixture of organic and inorganic molecules, such as a cell culture medium. In such complex fluids, chemical reactions induced by absorption of UV radiation by other species can result in other reactions with the actinometric compound in addition to the desired reaction of the actinometric compound to produce the actinometric photo-product, thereby interfering with calculation of the concentration of the photo-product and in turn the UV fluence received by the fluid.

Moreover, the addition of actinometric compounds to process fluids may not be permitted in certain applications. For example, the chemical composition of biopharmaceutical growth media (so-called "upstream" fluids) and biopharmaceutical production fluids (so-called "downstream" fluids) are tightly controlled and subject to rigorous validation and regulatory approval. For this reason, exogenous actinometers are typically not suitable to monitor UV fluence in fluids used in the course of biopharmaceutical production and purification.

There is therefore a need for an endogenous actinometric process by which the UV fluence delivered to a complex fluid (e.g., a cell culture medium) can be measured to ensure that such fluids have achieved a target level of disinfection.

SUMMARY OF THE INVENTION

It is an object of the present invention to obviate or mitigate at least one of the above-mentioned disadvantages of the prior art.

It is another object of the present invention to provide a novel method of determining the UV fluence received by a fluid.

It is yet another object of the present invention to provide a novel system for determining the UV fluence received by a fluid being treated in UV fluid treatment system.

Accordingly, in one of its aspects, the present invention provides A method of determining the UV fluence received by a fluid, the method comprising the steps of:
(a) irradiating the fluid at an unknown UV fluence;
(b) measuring the fluorescence of a test sample of the fluid after irradiation in Step (a) to produce a test signal proportional to the concentration of a prescribed fluorescent composition of matter comprised in the test sample;
(c) determining the value of the unknown UV fluence by comparing the test signal to a calibration curve of a control signal proportional to concentration of the prescribed fluorescent composition of matter in the fluid as a function of applied UV fluence.

In another of its aspects, the present invention provides a method determining the UV fluence received by a fluid, the method comprising the steps of:
(a) measuring the fluorescence of a control sample of the fluid comprising a prescribed fluorescent composition of matter prior to exposure to UV to determine a zero dose fluorescence ($F_c$) of the control sample;
(b) irradiating the fluid having at an unknown UV fluence;
(c) measuring the fluorescence of a test sample of the fluid comprising a prescribed fluorescent composition of matter after Step (b) to determine treated fluorescence ($F_u$) of the test sample; and
(d) determining the value of the unknown UV fluence by correlating $F_c$ and $F_u$ to a calibration curve of the concentration of the prescribed fluorescent composition of matter in the fluid as a function of applied UV fluence.

In yet another of its aspects, the present invention provides a system for determining the UV fluence received by a fluid being treated in UV fluid treatment system comprising at least one UV source, the system comprising:
(a) a radiation-transparent vessel for receiving a test sample of the fluid after irradiation of the fluid at an unknown UV fluence;
(b) a fluorometer for measuring the fluorescence of the test sample received in the radiation-transparent vessel to produce a test signal proportional to the concentration of a prescribed fluorescent composition of matter comprised in the test sample; and
(c) a controller configured to determine the value of the unknown UV fluence by comparing the test signal to a calibration curve of a control signal proportional to concentration of the prescribed fluorescent composition of matter in the fluid as a function of applied UV fluence.

Thus, the present inventors have developed a novel method and system for determining the UV fluence received by a fluid being treated in UV fluid treatment system. The novel method and system involve measure the fluorescence of a test sample of the fluid to determine an unknown UV fluence delivered to fluid being treated in the UV fluid treatment system. A particularly preferred embodiment of the present invention relates to application with a fluid that contains a fluorescent composition of matter (e.g., an organisms or a molecule) as an indigenous or endogenous component. The advantage of application to such a fluid is that no additional fluorescent component needs to be added to the test sample in order to determine the unknown UV fluence delivered to the fluid being treated in the UV fluid treatment system.

In one embodiment, the fluorescent composition of matter comprises a biological molecule such as a proteins and/or a peptide. As is known in the art, peptides are chains of amino acids and many are fluorescent due to the presence of tryptophan, tyrosine and/or phenylalanine. As is further known in the art, proteins are long chains of amino acids. Those that do fluoresce naturally generally do so because they contain the amino acid tryptophan. Green Fluorescent Protein (GFP) first isolated from jellyfish (Aequorea Victoria), has been engineered into many organisms including bacteria, yeast, and fish and is useful in the present method and system. As is known in the art, there are many engineered and natural variants of GFP, with various emission wavelengths (not just Green), temperature sensitivities, etc. and these are also useful in the present method and system.

In another embodiment, the fluorescent composition of matter may comprise an amino acid. Preferably, the amino acid is selected from the group consisting of tryptophan, tyrosine, phenylalanine and any mixture thereof.

Many enzymatic cofactors, such as FMN (a form of riboflavin), FAD, NADH and porphyrins, are also intrinsically fluorescent and these are useful in the present method and system.

In another embodiment, the fluorescent composition of matter used in the present method and system may comprise a non-biological compound. Such compounds are known in the art—see, for example, http://flowcyt.salk.edu/fluo.html.

BRIEF DESCRIPTION OF THE DRAWINGS

Embodiments of the present invention will be described with reference to the accompanying drawings, wherein like reference numerals denote like parts, and in which.

DETAILED DESCRIPTION OF THE PREFERRED EMBODIMENTS

Figure 1:
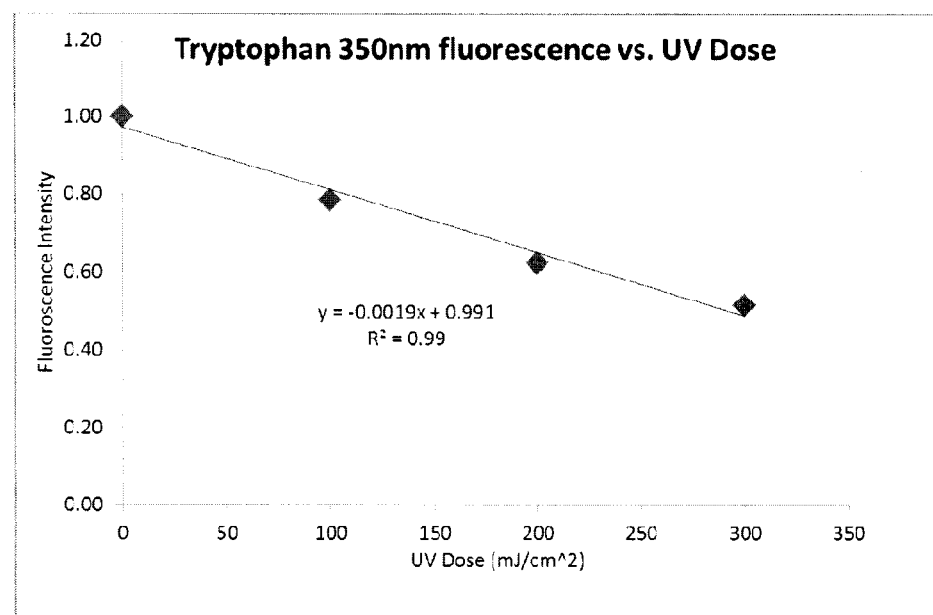
FIG. 1 illustrates a calibration curve of the measured fluorescence at the tryptophan emission wavelength of 350 nm as a function of UV fluence received by samples of the culture medium "Invitrogen CD-CHO" according to a preferred embodiment of the present invention.

Thus, in one of its aspects, the present invention relates to a method of determining the UV fluence received by a fluid, the method comprising the steps of: (a) irradiating the fluid at an unknown UV fluence; (b) measuring the fluorescence of a test sample of the fluid after irradiation in Step (a) to produce a test signal proportional to the concentration of a prescribed fluorescent composition of matter comprised in the test sample; and (c) determining the value of the unknown UV fluence by comparing the test signal to a calibration curve of a control signal proportional to concentration of the prescribed fluorescent composition of matter in the fluid as a function of applied UV fluence. Preferred embodiments of this method may include any one or a combination of any two or more of any of the following features:

- the fluid is an aqueous liquid;
- the fluid is water;
- the fluid is a cell culture medium;
- the cell culture medium comprises at least one member selected from the group consisting of fetal bovine serum, a growth factor, a buffering agent and any mixture thereof;
- the fluid is a blood product;
- the fluid is an aquaculture wastestream;
- the fluid is an aqueous liquid comprising a therapeutic;
- the fluid comprises a member selected from the group consisting of an antibody, a virus (active or inactive), a vaccine, an enzyme and any mixture thereof;
- the fluorescent composition of matter is added to the fluid prior to Step (a);
- the fluorescent composition of matter is endogenous to the fluid;
- the fluorescent composition of matter is indigenous to the fluid;
- the fluorescent composition of matter comprises an organism;
- the fluorescent composition of matter comprises a microorganism;
- the fluorescent composition of matter comprises a chemical compound;
- the fluorescent composition of matter comprises a protein or a peptide;
- the fluorescent composition of matter comprises an amino acid;
- the fluorescent composition of matter comprises tryptophan;
- the fluorescent composition of matter comprises tyrosine;
- Step (b) comprises subjecting the test sample to fluorescence spectroscopy;
- Step (b) comprises exposing the test sample to radiation having, in respect of the prescribed fluorescent composition of matter, at least one excitation wavelength and detecting at least one emission wavelength;
- the at least one excitation wavelength is in the range of from about 280 nm to about 800 nm;
- the at least one excitation wavelength is in the range of from about 280 nm to about 340 nm;
- the at least one emission wavelength is in the range of from about 300 nm to about 450 nm;
- Step (a) is conducted at one or more wavelengths in the range of from about 100 nm to about 400 nm;
- Step (a) is conducted at one or more wavelengths in the range of from about 100 nm to about 315 nm;
- Step (a) is conducted at one or more wavelengths in the range of from about 100 nm to about 280 nm;
- the method comprises the additional steps of: (d) comparing the value of the unknown UV fluence determined in Step (c) with a predetermined fluence which achieves a prescribed level of inactivation of at least one microorganism contaminant in the fluid when the fluid is being treated in a fluid treatment system that comprises at least one UV radiation source; and (e) adjusting one or more operating parameters (e.g., the output of the at least one UV radiation source) when the value of the unknown UV fluence of determined in Step (c) deviates from the predetermined fluence beyond a predetermined limit;
- the method comprises the additional steps of: (d) comparing the value of the unknown UV fluence determined in Step (c) with a predetermined fluence which achieves a prescribed level of inactivation of at least one microorganism contaminant in the fluid when the fluid is being treated in a fluid treatment system that comprises at least one UV radiation source; and (e) actuating an alarm when the value of the unknown UV fluence of determined in Step (c) deviates from the predetermined fluence beyond a predetermined limit;
- Step (e) comprises actuating an audio signal or a visual signal; and/or
- Step (e) comprises actuating an audio signal and a visual signal.

In another of its aspects, the present invention relates to a method determining the UV fluence received by a fluid, the method comprising the steps of: (a) measuring the fluorescence of a control sample of the fluid comprising a prescribed fluorescent composition of matter prior to exposure to UV to determine a zero dose fluorescence ($F_c$) of the control sample; (b) irradiating the fluid having at an unknown UV fluence; (c) measuring the fluorescence of a test sample of the fluid comprising a prescribed fluorescent composition of matter after Step (b) to determine treated fluorescence ($F_u$) of the test sample; and (d) determining the value of the unknown UV fluence by correlating $F_c$ and $F_u$ to a calibration curve of the concentration of the prescribed fluorescent composition of matter in the fluid as a function of applied UV fluence. Preferred embodiments of this method may include any one or a combination of any two or more of any of the following features:

- the fluid is an aqueous liquid;
- the fluid is water;
- the fluid is a cell culture medium;
- the cell culture medium comprises at least one member selected from the group consisting of fetal bovine serum, a growth factor, a buffering agent and any mixture thereof;
- the fluid is a blood product;
- the fluid is an aquaculture wastestream;
- the fluid is an aqueous liquid comprising a therapeutic;
- the fluid comprises a member selected from the group consisting of an antibody, a virus (active or inactive), a vaccine, an enzyme and any mixture thereof;
- the fluorescent composition of matter is added to the fluid prior to Step (a);
- the fluorescent composition of matter is endogenous to the fluid;
- the fluorescent composition of matter is indigenous to the fluid;
- the fluorescent composition of matter comprises an organism;
- the fluorescent composition of matter comprises a microorganism;
- the fluorescent composition of matter comprises a chemical compound;
- the fluorescent composition of matter comprises a protein or a peptide;
- the fluorescent composition of matter comprises an amino acid;
- the fluorescent composition of matter comprises tryptophan;

the fluorescent composition of matter comprises tyrosine;
Step (a) comprises subjecting the control sample to fluorescence spectroscopy.
Step (a) comprises exposing the control sample to radiation having, in respect of the prescribed fluorescent composition of matter, at least one excitation wavelength and detecting at least one emission wavelength;
Step (c) comprises subjecting the test sample to fluorescence spectroscopy;
Step (c) comprises exposing the test sample to radiation having, in respect of the prescribed fluorescent composition of matter, at least one excitation wavelength and detecting at least one emission wavelength;
the at least one excitation wavelength is in the range of from about 280 nm to about 800 nm;
the at least one excitation wavelength is in the range of from about 280 nm to about 340 nm
the at least one emission wavelength is in the range of from about 300 nm to about 450 nm
Step (b) is conducted at one or more wavelengths in the range of from about 100 nm to about 400 nm.
(b) is conducted at one or more wavelengths in the range of from about 100 nm to about 315 nm
Step (b) is conducted at one or more wavelengths in the range of from about 100 nm to about 280 nm
the method comprise the additional steps of: (e) comparing the value of the unknown UV fluence determined in Step (d) with a predetermined fluence which achieves a prescribed level of inactivation of at least one microorganism contaminant in the fluid when the fluid is being treated in a fluid treatment system that comprises at least one UV radiation source; and (f) adjusting one or more operating parameters (e.g., the output of the at least one UV radiation source) when the value of the unknown UV fluence of determined in Step (c) deviates from the predetermined fluence beyond a predetermined limit;
the method comprises the additional steps of: (e) comparing the value of the unknown UV fluence determined in Step (c) with a predetermined fluence which achieves a prescribed level of inactivation of at least one microorganism contaminant in the fluid when the fluid is being treated in a fluid treatment system that comprises at least one UV radiation source; and (f) actuating an alarm when the value of the unknown UV fluence of determined in Step (c) deviates from the predetermined fluence beyond a predetermined limit;
Step (f) comprises actuating an audio signal or a visual signal; and/or
Step (f) comprises actuating an audio signal and a visual signal.

In yet another of its aspects, the present invention relates to a system for determining the UV fluence received by a fluid being treated in UV fluid treatment system comprising at least one UV source, the system comprising: (a) a radiation-transparent vessel for receiving a test sample of the fluid after irradiation of the fluid at an unknown UV fluence; (b) a fluorometer for measuring the fluorescence of the test sample received in the radiation-transparent vessel to produce a test signal proportional to the concentration of a prescribed fluorescent composition of matter comprised in the test sample; and (c) a controller configured to determine the value of the unknown UV fluence by comparing the test signal to a calibration curve of a control signal proportional to concentration of the prescribed fluorescent composition of matter in the fluid as a function of applied UV fluence.

Preferred embodiments of this method may include any one or a combination of any two or more of any of the following features:
the controller further comprises a memory element in which the calibration curve is stored;
the fluorometer is configured to expose the test sample comprised in the vessel to radiation having, in respect of the prescribed fluorescent composition of matter, at least one excitation wavelength and to detect at least one emission wavelength;
the at least one excitation wavelength is in the range of from about 280 nm to about 340 nm;
the at least one excitation wavelength is in the range of from about 280 nm to about 800 nm
the at least one emission wavelength is in the range of from about 300 nm to about 450 nm;
the controller is configured to carry out the following steps: comparing the value of the unknown UV fluence with a predetermined fluence which achieves a prescribed level of inactivation of at least one microorganism contaminant in the fluid when the fluid is being treated in the UV treatment system; and adjusting one or more operating parameters (e.g., the output of the at least one UV radiation source) when the value of the unknown UV fluence deviates from the predetermined fluence beyond a predetermined limit.
the controller is configured to carry out the following steps: comparing the value of the unknown UV fluence with a predetermined fluence which achieves a prescribed level of inactivation of at least one microorganism contaminant in the fluid when the fluid is being treated in the UV treatment system; and actuating an alarm when the value of the unknown UV fluence deviates from the predetermined fluence beyond a predetermined limit;
the alarm is configured to actuate an audio signal or a visual signal; and/or
the alarm is configure to actuate an audio signal and a visual signal.

The present method and system comprise the use of a calibration curve in order to control a UV system to achieve a target UV dose delivered to a process fluid. Such a calibration curve may be obtained by irradiating samples of the process fluid to discrete, known doses of UV radiation, and then measuring the fluorescence of one or more compounds in the irradiated samples.

In a preferred embodiment of the present system, this calibration curve is incorporated into the memory or software of a controller. In a preferred aspect, the controller has as an input the signal from a fluorometer that is used to continuously or periodically measure the fluorescence of a process fluid that is being treated using UV radiation. This may be executed continuously, using a side-stream or wastestream from the treated process fluid or it may be executed periodically, using so-called grab samples obtained manually or automatically through, for example, sampling valves.

Based on the signal from the fluorometer, and comparing that signal against the calibration curve, the controller may adjust one or more operating parameters of the UV system in order to achieve a desired UV dose in the process fluid. Non-limiting examples of such operating parameters include flow rate of the process fluid, intensity or power level of one or more UV lamps, the number of lamps in operation, the state of control valves used to incorporate more or fewer UV systems into the treatment train, or other operating variables of the UV system. The controller may consist of a Programmable Logic Controller, a computer or other similar device.

The device may also incorporate a dose (high dose and/or low dose) alarm. If the range of control of the UV system is not sufficient to reach the target dose in the fluid, the device will provide a signal that can be used to perform actions such as: shutting down the flow of process fluid; providing a visual or auditory alarm indicating a failure to deliver the target Dose; sending a text, email or other notification to a user.

Fluorometers are known to those skilled in the art. Nonetheless, the preferred fluorometer will consist of a source of incident radiation in the range of from about 200 nm to about 400 nm, with an optical path suitable for irradiating a sample of fluid. The fluorometer will preferably include a means of monitoring the intensity of the source. Preferably, the fluorometer will further include an optical radiation sensor suitable for measuring radiation at one or more wavelengths in the range of from about 250 to about 500 nm.

The sensor will preferably be configured to receive radiation from a direction substantially different from the forward path of the incident radiation. This direction may include a direction substantially perpendicular to that of the incident radiation, or may include a direction opposite to the incident radiation. This arrangement minimizes the amount of the incident radiation beam that is received by the sensor, thus allowing better response to the fluorescence emitted by the sample. The sensor may incorporate optical filters to ensure that primarily the desired wavelength range is detected and other wavelengths are rejected, and may incorporate a spectral detector able to respond to discrete wavelengths, so that emission from more than one compound may be discriminated.

The accuracy of the method can be improved by developing and utilizing calibration curves for more than one compound and measuring the fluorescence signal from more than one compound in the process fluid. For example tryptophan and tyrosine are both photosensitive, so that their concentration and resulting fluorescence will change with UV dose, and they have distinct peak emission wavelengths of 355 nm and 303 nm, respectively. Random errors in measurement of fluorescence for the two compounds will not be correlated and will tend to cancel each other. Quantifying emission from each of these compounds independently can increase the accuracy of the method and device.

The present method may also comprise the additional step of clarifying the irradiated fluid medium through the use of a suitable precipitant, including for example acidified lead acetate. Addition of a suitable precipitant will result in proteins, amino acids or other species precipitating from solution thereby clarifying the supernatant and reducing interference in fluorescence or absorbance measurements from such compounds.

Embodiments of the present invention will now be actually demonstrated with reference to the following examples which are provided for illustrative purposes only and should not be used to limit or construe the invention.

Example 1

According to a preferred embodiment of the present invention, the fluid is a commercial cell culture medium, "Invitrogen CD-CHO". One component of this cell culture medium is tryptophan, an essential amino acid present in most cell culture media. Tryptophan is known to be degraded by UV radiation, and as such its concentration in a fluid will decrease with increasing UV fluence.

Tryptophan is also a fluorescent species, whose fluorescence can be measured at about 360 nm when excited at about 275 nm. The fluorescence of tryptophan is proportional to the intensity of the excitation and the concentration of tryptophan.

As noted, tryptophan concentration in a fluid decreases with UV fluence received by that fluid. In turn, the fluorescence signal from tryptophan in that fluid will also decrease with UV fluence, thereby providing a direct measure of the UV fluence received by the fluid.

According to the present example, fluorescence spectroscopy was used to quantify the concentration of tryptophan present in a sample of the cell culture medium irradiated with an unknown UV fluence, which was in turn compared against a previously-developed calibration curve to correlate fluorescence intensity with UV fluence of the fluid.

5 mL samples of Invitrogen CD-CHO were first irradiated under continuous stirring with discrete, known UV fluences in the range of 100-300 mJ/cm$^2$ using a "Collimated Beam" device incorporating a low-pressure mercury lamp emitting at 254 nm. This apparatus is known to provide uniform, quantified irradiation to liquid samples, and associated methods have been developed and standardized in the field of water disinfection (Bolton, J R and Linden, K G, (2003)). Standardization of Methods for Fluence (UV Dose) Determination in Bench-Scale UV Experiments, *Journal of Environmental Engineering*, 129(3), 209-215.

A control sample of the fluid which was not irradiated was retained.

The fluorescence signal of tryptophan was then measured at 350 nm in both the irradiated samples and the control sample to develop a calibration curve to correlate fluorescence with UV fluence. The test results presented in FIG. 1 show the calibration curve for the measured fluorescence at the tryptophan emission wavelength of 350 nm as a function of the UV fluence received by these samples.

Thereafter, a test sample of the Invitrogen CD-CHO growth medium was irradiated with an unknown UV fluence.

The fluorescence signal $F_c$ of a non-irradiated control sample of the Invitrogen CD-CHO growth medium was measured, and the fluorescence signal $F_u$ of the test sample of the Invitrogen CD-CHO growth medium irradiated with an unknown UV fluence was measured, both at the tryptophan emission wavelength of 350 nm. The ratio of these fluorescence signals ($F_u/F_c$) was calculated as 0.6. The UV fluence received by the test sample was then calculated according to the calibration curve equation shown in FIG. 1 as $(0.6-0.991)/-0.0019=206$ mJ/cm$^2$.

Figure 2:
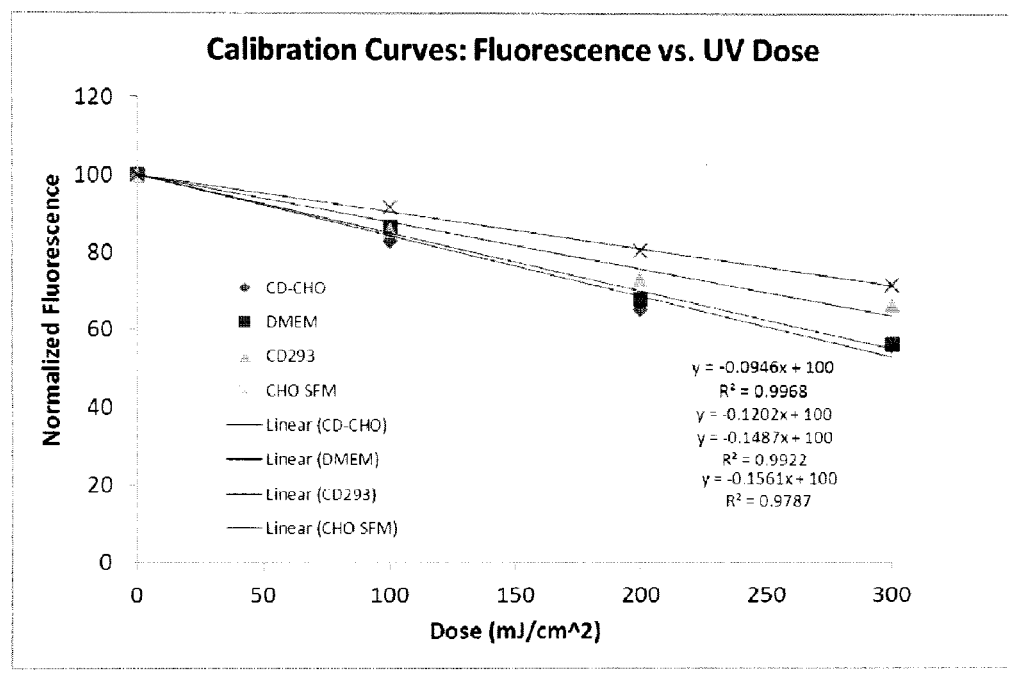
FIG. 2 illustrates calibration curves of the measured (normalized) fluorescence at the tryptophan emission wavelength of 350 nm as a function of UV fluence received by samples of four common culture media: "Invitrogen CD-CHO", "DMEM F12", "CHO SFM II", and "CD-293" according to a preferred embodiment of the present invention.

Calibration curves of the type described above based on the fluorescence of tryptophan have been developed for many different cell culture media according to the technique described above, including Invitrogen CD-CHO, DMEM F12, CHO SFM II, and CD-293. Calibration curves showing normalized fluorescence plotted against UV fluence (where fluorescence is normalized to a value of 100 at zero UV fluence) are shown in FIG. 2.

Importantly and advantageously, in a preferred embodiment, the present method for determining an unknown UV fluence received by a cell culture medium does not require the addition of any exogenous chemicals and does not otherwise alter or damage the intrinsic properties of the cell culture medium.

Moreover, the method may be customized for any fluorescent species typically present in the cell culture medium whose concentration correlates to UV fluence (including, for example, the amino acids tyrosine, tryptophan, phenylalanine, the B-vitamin riboflavin and the like) by adjusting the excitation and emission wavelengths in the steps of measuring the fluorescence of the samples.

While the examples provided relate to determination of UV fluence received by cell culture media, the methods described herein could be applied to UV treatment of any fluid containing fluorescent composition of matter as described above.

While this invention has been described with reference to illustrative embodiments and examples, the description is not intended to be construed in a limiting sense. Thus, various modifications of the illustrative embodiments, as well as other embodiments of the invention, will be apparent to persons skilled in the art upon reference to this description. It is therefore contemplated that the appended claims will cover any such modifications or embodiments.

All publications, patents and patent applications referred to herein are incorporated by reference in their entirety to the same extent as if each individual publication, patent or patent application was specifically and individually indicated to be incorporated by reference in its entirety.

What is claimed is:

1. A method of determining the UV fluence received by a fluid, the method comprising the steps of:
   (a) irradiating the fluid at an unknown UV fluence;
   (b) measuring the fluorescence of a test sample of the fluid after irradiation in Step (a) to produce a test signal proportional to the concentration of a prescribed fluorescent composition of matter comprised in the test sample; and
   (c) determining the value of the unknown UV fluence by comparing the test signal to a calibration curve of a control signal proportional to concentration of the prescribed fluorescent composition of matter in the fluid as a function of applied UV fluence.

2. The method defined in claim 1, wherein the fluid is an aqueous liquid.

3. The method defined in claim 1, wherein the fluid is a cell culture medium.

4. The method defined in claim 3, wherein the cell culture medium comprises at least one member selected from the group consisting of fetal bovine serum, a growth factor, a buffering agent and any mixture thereof.

5. The method defined in claim 1, wherein the fluid is a blood product.

6. The method defined in claim 1, wherein the fluid is an aqueous liquid comprising a therapeutic.

7. The method defined in claim 1, wherein the fluid comprises a member selected from the group consisting of an antibody, a virus (active or inactive), a vaccine, an enzyme, and any mixture thereof.

8. The method defined in 1, wherein the prescribed fluorescent composition of matter is added to the fluid prior to Step (a).

9. The method defined in claim 1, wherein the prescribed fluorescent composition of matter is indigenous to the fluid.

10. The method defined in claim 1, wherein the prescribed fluorescent composition of matter comprises an amino acid.

11. The method defined in claim 1, wherein the prescribed fluorescent composition of matter comprises tryptophan.

12. The method defined in claim 1, wherein the prescribed fluorescent composition of matter comprises tyrosine.

13. The method defined in claim 1, wherein Step (b) comprises subjecting the test sample to fluorescence spectroscopy.

14. The method defined in claim 1, wherein Step (b) comprises exposing the test sample to radiation having, in respect of the prescribed fluorescent composition of matter, at least one excitation wavelength and detecting at least one emission wavelength.

15. The method defined in claim 1, wherein Step (a) is conducted at one or more wavelengths in the range of from about 100 nm to about 400 nm.

16. The method defined in claim 1, comprising the additional steps of:
   (d) comparing the value of the unknown UV fluence determined in Step (c) with a predetermined fluence which achieves a prescribed level of inactivation of at least one microorganism contaminant in the fluid when the fluid is being treated in a fluid treatment system that comprises at least one UV radiation source; and
   (e) adjusting one or more operating parameters (e.g., the output of the at least one UV radiation source) when the value of the unknown UV fluence of determined in Step (c) deviates from the predetermined fluence beyond a predetermined limit.

17. The method defined in claim 1, comprising the additional steps of:
   (d) comparing the value of the unknown UV fluence determined in Step (c) with a predetermined fluence which achieves a prescribed level of inactivation of at least one microorganism contaminant in the fluid when the fluid is being treated in a fluid treatment system that comprises at least one UV radiation source; and
   (e) actuating an alarm when the value of the unknown UV fluence of determined in Step (c) deviates from the predetermined fluence beyond a predetermined limit.

18. The method defined in claim 17, wherein Step (e) comprises actuating an audio signal or a visual signal.

19. A method determining the UV fluence received by a fluid, the method comprising the steps of:
   (a) measuring the fluorescence of a control sample of the fluid comprising a prescribed fluorescent composition of matter prior to exposure to UV to determine a zero dose fluorescence ($F_c$) of the control sample;
   (b) irradiating the fluid having at an unknown UV fluence;
   (c) measuring the fluorescence of a test sample of the fluid comprising a prescribed fluorescent composition of matter after Step (b) to determine treated fluorescence ($F_u$) of the test sample; and
   (d) determining the value of the unknown UV fluence by correlating $F_c$ and $F_u$ to a calibration curve of the concentration of the prescribed fluorescent composition of matter in the fluid as a function of applied UV fluence.

20. A system for determining the UV fluence received by a fluid being treated in UV fluid treatment system comprising at least one UV source, the system comprising:
   (a) a radiation-transparent vessel for receiving a test sample of the fluid after irradiation of the fluid at an unknown UV fluence;
   (b) a fluorometer for measuring the fluorescence of the test sample received in the radiation-transparent vessel to produce a test signal proportional to the concentration of a prescribed fluorescent composition of matter comprised in the test sample; and
   (c) a controller configured to determine the value of the unknown UV fluence by comparing the test signal to a calibration curve of a control signal proportional to concentration of the prescribed fluorescent composition of matter in the fluid as a function of applied UV fluence.

* * * * *